US006281396B1

(12) United States Patent
Manzer et al.

(10) Patent No.: US 6,281,396 B1
(45) Date of Patent: *Aug. 28, 2001

(54) FLUOROCARBON PURIFICATION PROCESS

(75) Inventors: Leo Ernest Manzer; V. N. Mallikarjuna Rao, both of Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/514,373

(22) Filed: Aug. 11, 1995

Related U.S. Application Data

(63) Continuation of application No. 08/190,709, filed on Feb. 2, 1994, now Pat. No. 5,461,177, which is a continuation of application No. 07/592,173, filed on Oct. 9, 1990, now abandoned, which is a continuation of application No. 07/417,650, filed on Oct. 4, 1989, now abandoned.

(51) Int. Cl.$^7$ ............................ C07K 17/38; C07C 17/00
(52) U.S. Cl. ......................... 570/177; 570/168; 570/178
(58) Field of Search .................................. 570/168, 177, 570/178

(56) References Cited

U.S. PATENT DOCUMENTS

| | | | |
|---|---|---|---|
| 2,999,885 | 9/1961 | Heberling | 260/648 |
| 3,004,075 | 10/1961 | Marcall | 260/648 |
| 3,218,363 | 11/1965 | Haszeldine | 260/648 |
| 3,258,500 | 6/1966 | Swamer et al. | 260/653.7 |
| 3,381,041 | 4/1968 | Kometani et al. | 260/653 |
| 3,696,156 | 10/1972 | Weeks | 260/68 F |
| 3,873,629 | 3/1975 | Jones | 260/653 |
| 3,947,558 | 3/1976 | van Eijl | 423/483 |
| 3,976,447 | 8/1976 | Merchant et al. | 55/71 |
| 4,129,603 | 12/1978 | Bell | 260/653 |
| 4,158,675 | 6/1979 | Potter | 260/653.7 |
| 4,209,470 | 6/1980 | Lorquet | 260/652 |
| 4,258,225 | 3/1981 | Feiring | 570/168 |
| 4,374,289 | 2/1983 | Van Der Puy et al. | 570/168 |
| 4,766,260 | 8/1988 | Manzer et al. | 570/168 |
| 4,792,643 | 12/1988 | Soboley | 570/168 |
| 5,444,171 | 8/1995 | Ohno et al. | 570/177 |

FOREIGN PATENT DOCUMENTS

| | | |
|---|---|---|
| 160 718 | 2/1984 | (DE) . |
| 1 031 409 | 2/1966 | (GB) . |

OTHER PUBLICATIONS

Hudlicky, M., *Chemistry of Organic Fluorine Compounds*, 2nd (rev.) edition, John Wiley, NY, p. 727 (1976).

Hine, J. *Physical Organic Chemistry*, 2nd edition, McGraw–Hill, NY pp. 484–488 (1962).

*Primary Examiner*—Alan Siegel

(57) ABSTRACT

A halocarbon product made from the reaction of excess hydrogen fluoride with a halocarbon, containing excess hydrogen fluoride as an azeotrope is purified by fluorination in the presence of additional halocarbon or halo-olefin.

20 Claims, No Drawings

FLUOROCARBON PURIFICATION PROCESS

This is a continuation division of application Ser. No. 08/190,709 filed Feb. 2. 1994, now U.S. Pat. No. 5,461,177 allowed, which is a continuation of application Ser. No. 07/592,173 filed Oct. 9. 1990, now abandoned, which in turn is a continuation of application Ser. No. 07/417,650 filed on Oct. 4, 1989, now abandoned.

BACKGROUND OF THE INVENTION

This invention relates to a process for the purification of fluorocarbons and the recovery of hydrogen fluoride used in their manufacture.

In many processes for making fluorocarbons in order to obtain an adequate degree of conversion of the starting halocarbon, it is necessary to employ an excess of hydrogen fluoride. It is highly desirable for economic reasons to recover this excess hydrogen fluoride, e.g., so it can be recycled.

Many processes have been developed for this purpose. However, since some of the hydrogen fluoride may be combined with the product as an azeotrope or be present in a slight excess to the product, in many cases it is difficult to remove. Neutralization of such hydrogen fluoride leads to waste disposal problems and environmental concerns. More complicated methods of separation lead to additional capital investment because hydrogen fluoride is a hazardous and difficult to handle material.

Furthermore, the recovery of the hydrogen fluoride is complicated by the unsaturated compounds which may also be present as impurities. These materials are particularly undesirable as contaminants as they may be toxic and for most uses their concentrations in the saturated products must be lowered to as low a level as is practically possible. Distillation and other conventional physical methods which may be used to lower the concentrations of unsaturated products are generally ineffective if the boiling points are too close, and are generally too costly. Therefore, various chemical treatments have been proposed.

None of these prior processes is entirely satisfactory from a commercial viewpoint. The aqueous alkaline metal permanganate treatments of the art require that the halocarbon products exiting the treatment medium be dried (separated from its entrained water) before further refining, which adds to the expense of the treatment. Moreover, where saturated halohydrocarbon products are being treated, the possibility exists that some of the valuable saturated material could be lost to the alkaline oxidative medium along with the unsaturated impurities.

Thus, an effective process must not only recover the combined hydrogen fluoride but must also take care of any unsaturated impurities present.

The process of the invention efficiently utilizes the combined hydrogen fluoride by reacting it with additional starting material or any other suitable halocarbon or halo-olefin and also with the olefin which is in the reaction product that is to be treated.

SUMMARY OF THE INVENTION

This invention provides for a process for the reduction of the hydrogen fluoride content of a halocarbon product made from the reaction of hydrogen fluoride with a halocarbon by reacting the excess hydrogen fluoride, which is substantially combined as an azeotrope, with additional halocarbon or halo-olefin, over a fluorination catalyst under fluorination conditions. The halocarbon product containing the hydrogen fluoride may also contain olefinic impurities which are converted to saturated compounds during the fluorination.

DETAIL OF THE INVENTION

The invention may be applied to the reduction of the hydrogen fluoride content of saturated halocarbon products and mixtures thereof, prepared by reaction with hydrogen fluoride and which contain one or more fluorine atoms in the molecule, and if they contain more than one carbon atom may be contaminated with olefinic impurities. Included are chlorofluoro- and fluorohydrocarbons composed of: carbon, hydrogen, chlorine and fluorine, and carbon, hydrogen and fluorine. The saturated halocarbons and/or mixtures thereof preferably contain 1 to 6 carbon atoms, more preferably 1 to 3, most preferably 1 to 2 because of their greater commercial importance.

The saturated halocarbons and/or mixtures thereof include cyclic as well as acyclic compounds represented by the empirical formula $C_aH_bCl_cF_d$ where a is an integer from 1 to 6, b, c and d are integers from 1 to 13, provided that b+c+d equals 2a+2 when the compound is acyclic and equals 2a when the compound is cyclic.

In a preferred embodiment the halocarbons are acyclic chlorofluorohydrocarbons, represented by the above empirical formula where a is 1 to 3, b and c are 1 to 7 and is 1 to 7.

In another preferred embodiment the halocarbons are acyclic fluorohydrocarbons represented by the above empirical formula where a is 1 to 3, b is 1 to 7, c is 0, and d is 1 to 7, and b+d equals 4 when a equals 1, equals 6 when a equals 2, and equals 8 when a equals 3.

Representative saturated halocarbons that can be treated in accordance with the method of the invention include chlorofluorohydrocarbons such as $CHClF_2$, $CF_3CHCl_2$ and $CF_3CHClF$; and fluorohydrocarbons such as $CHF_2CHF_2$ and $CF_3CH_2F$.

The above saturated halocarbons are produced by processes that result in the product containing excess hydrogen fluoride, usually combined as an azeotrope. The composition of this azeotrope will vary depending on the product halocarbon. In some embodiments, if the excess hydrogen fluoride is not all combined to form an azeotrope, the product mixture can first be subjected to a conventional separation process to remove the uncombined hydrogen fluoride and other easily separated material. In other embodiments, the product mixture will contain unsaturated impurities. By easily separated materials is meant materials having boiling points sufficiently far apart to make an economic separation feasible, e.g., distillation.

As set forth above, the product mixture contains the excess hydrogen fluoride as an azeotrope. This is an azeotrope of hydrogen fluoride with the halocarbon of the formula $C_aH_bCl_cF_d$ where a, b, c and d are as previously defined.

The product mixture after separation of its easily separated components, is then fed into a reactor where it is contacted with additional halocarbon under fluorinating conditions in the presence of a fluorination catalyst.

The additional halocarbon which is reacted with the excess hydrogen fluoride azeotrope can be represented by the empirical formula $C_aH_bCl_cF_d$ where a is an integer from 1 to 6, b and a are integers from 0 to 13, and a is an integer from 1 to 13, provided that b+c+d equals 2a+2 when the compound is acyclic and equals 2a when the compound is cyclic.

The additional halo-olefin which is reacted with the excess hydrogen fluoride azeotrope can be represented by the empirical formula $C_aH_bCl_cF_d$ where a is an integer from 2 to 6, b and d are integers from 0 to 11, and c is an integer from 1 to 11, provided that b+c+d equals 2a when the compound is acyclic and equals 2a−2 when the compound is cyclic.

Conventional fluorination catalysts and conditions can be used in the process of the invention.

The catalytic systems needed to effect the reaction of the product halocarbon/hydrogen fluoride mixture with an additional halocarbon can employ both vapor and liquid phase approaches. Examples of vapor phase catalysts and procedures for their use in fluorination reactions are described in U.S. Pat. Nos. 4,766,260, 3,258,500, and in the references cited therein. Examples of liquid phase catalysts and procedures for their use in fluorination reactions are described in U.S. Pat. Nos. 4,374,289, 4,258,225, and in the references cited therein.

The reaction vessel is constructed from materials which are resistant to the action of hydrogen halide such as Hastelloy® nickel alloy or Inconel® nickel alloy.

The purified halocarbons are useful as refrigerants, blowing agents and solvents.

A process is provided in accordance with this invention for the reduction of the hydrogen fluoride content of fluorocarbons by reacting excess hydrogen fluoride with a halocarbon comprising: (a) feeding a halocarbon product mixture containing an azeotrope of hydrogen fluoride with at least one compound of the formula $C_aH_bCl_cF_d$, where a is 1 to 6, b is 1 to 13, c is 1 to 13 and d is 1 to 13, provided that b+c+d equals 2a+2 when the compound is acyclic and 2a when it is cyclic, into a reactor; (b) contacting the azeotrope of (a) with: (i) an amount of a compound of the formula $C_aH_bCl_cF_d$ where a is 1 to 6, b is 0 to 13, c is 1 to 13, and d is 0 to 13, provided that b+c+d equals 2a+2 when the compound is acyclic and 2. when it is cyclic; or, (ii) an amount of a halo-olefin of the formula $C_aH_bCl_cF_d$ where a is 2 to 6, b is 0 to 11, c is 1 to 11, and d is 0 to 11, provided b+c+d equals 2a when the compound is acyclic and 2a−2 when it is cyclic; the amount being in excess of the amount of hydrogen fluoride in the azeotrope with a fluorination catalyst under fluorinating conditions. A halocarbon product made from the reaction of excess hydrogen fluoride as an azeotrope can thus be purified by fluorination in the presence of additional halocarbons or halo-olefin.

As an example of the process, chlorodifluoromethane can be produced by the reaction of $CHCl_3$ and hydrogen fluoride over a fluorination catalyst such as $SbCl_5$, for example as described in M. Hudlicky, "Chemistry of Organic Fluorine Compounds," 2nd (Revised) Ed., John Wiley, N.Y., 1976, p. 727. The reaction product stream contains hydrogen fluoride, $CHClF_2$, HCl, $CHCl_2F$, and minor amounts of other products. After separation of HCl and most of the excess hydrogen fluoride, the stream containing $CHClF_2$ and the combined hydrogen fluoride is reacted with an additional halocarbon in a molar amount greater than the hydrogen fluoride contained in the $CHClF_2$/hydrogen fluoride product stream to afford more highly fluorinated halocarbons. Preferably the additional halocarbon is $CHCl_3$ and the more highly fluorinated halocarbons produced are $CHCl_2F$ and $CHClF_2$.

2,2-Dichloro-1,1,1-trifluoroethane ($CF_3CHCl_2$) and 1,1,1,2-tetrafluoro-2-chloroethane ($CF_3CHClF$) can be produced by the reaction of hydrogen fluoride and tetrachloroethene ($CCl_2=CCl_2$) in the presence of a selected metal on a high fluorine content alumina support; for example as described in U.S. Pat. No. 4,766,260. The reaction product stream contains hydrogen fluoride, HCl, $CCl_2CCl_2$, $CF_3CHCl_2$, $CF_3CHClF$ and $CF_3CHF_2$. After separation of HCl, $CCl_2=CCl_2$, $CF_3CHF_2$ and most of the excess hydrogen fluoride, the stream containing $CF_3CHCl_2$, $CF_3CHClF$ and the combined hydrogen fluoride or optionally separate products containing $CF_3CHCl_2$ and combined hydrogen fluoride and $CF_3CHClF$ and combined hydrogen fluoride is reacted with additional halocarbon in a molar amount greater than the hydrogen fluoride contained in the $CF_3CHCl_2$/$CF_3CHClF$/hydrogen fluoride or $CF_3CHCl_2$/hydrogen fluoride and $CF_3CHClF$/hydrogen fluoride product streams to afford more highly fluorinated halocarbons. Preferably the additional halocarbon is $CCl_2=CCl_2$ and the more highly fluorinated halocarbons produced are $CF_3CHClF$, $CF_3CHCl_2$, $CF_2ClCHCl_2$ and $CFCl_2CHCl_2$.

In a similar manner, as described above for $CHClF_2$/hydrogen fluoride and $CF_3CHCl_2$/$CF_3CHClF$/hydrogen fluoride, $CF_3CHCl_2$/hydrogen fluoride and $CF_3CHClF$/hydrogen fluoride products, other halocarbon/hydrogen fluoride mixtures may be treated to reduce the hydrogen fluoride concentration of the product stream.

The process will be further illustrated by the following Examples.

EXAMPLES

General Experimental Procedure for Liquid-Phase Reactions

The reactor consisted of a 100 mL high pressure cylinder made of Monel® nickel alloy or Inconel® nickel alloy containing a magnetic stirrer and an internal thermocouple. A condenser and a back-pressure regulator, connected to an optional on-line analytical system, were mounted on top of the reactor. Suitable inlet and exit lines were present to allow for admission of reactants and withdrawal of products.

To the reactor was charged $TaF_5$ in the desired amount. The reactor was then cooled to −78° C. and the ambient atmosphere removed under vacuum. The reactants were added to the reactor, which was then pressurized with nitrogen to the desired pressure while still cold. The reactants were gradually heated to the desired operating temperature with stirring, with external heat provided by an oil bath. The back-pressure regulator was set to the desired operating pressure prior to heating the reactor.

At the completion of the reaction, the reactor contents were cooled to room temperature and the product composition determined by gas chromatography. The percentages reported in the Examples are in area % unless otherwise indicated.

Example 1

Reaction of Hydrogen Fluoride/1,1,1,2-Tetrafluoroethane with Trichloroethene The General Experimental Procedure for liquid-phase reactions was followed using $TaF_5$ (3.0 g, 0.011 mol), $CF_3CH_2F$ (25 mL, 0.30 mol), anhydrous hydrogen fluoride (1.25 mL, 0.063 mol), the HF and $CF_3CH_2F$ amounts were selected so as to simulate an azeotropic composition, and $CHCl=CCl_2$ (10.0 g, 0.076 mol). The reactor was pressurized to 200 psig when cold (−78° C.) with nitrogen. The back pressure regulator was set for 500 psig. The contents of the reactor were stirred and heated to 93–95° C. for about one hour. At run's end the reactor contents were cooled to room temperature and discharged onto ice. $CF_3CH_2F$ was allowed to evaporate and the lower organic layer separated and analyzed to obtain the following on a $CF_3CH_2F$-free basis; 19.1% $CClF_2CH_2Cl$, 38.3% $CCl_2FCH_2Cl$, 5.8% $CCl_3CH_2Cl$ and 34.3% $CHCl=CCl_2$. Small amounts (<2.5%) of other unidentified products were present.

These results show that the hydrogen fluoride which is combined with $CF_3CH_2F$ does indeed react with $CHCl=CCl_2$ leaving a vapor stream enriched in $CF_3CH_2F$.

Example 2

Reaction of Hydrogen Fluoride/1,1,1,2-Tetrafluoroethane with Trichloroethene

The General Experimental Procedure for liquid-phase reactions was followed using $TaF_5$ (0.5 g, 0.002 mol), $CF_3CH_2F$ (25 mL, 0.30 mol), anhydrous hydrogen fluoride (1.25 mL, 0.063 mol), the HF and $CF_3CH_2F$ amounts were selected so as to simulate an azeotropic composition, and $CHCl=CCl_2$ (10.0 g, 0.076 mol). The reactor was pressurized to 200 psig when cold (−78° C.) with nitrogen. The back pressure regulator was set for 500 psig. The contents of the reactor were stirred and heated to 96–104° C. for about thirty mi nutes. At run's end the reactor contents were cooled to room temperature and discharged onto ice. Most of the $CF_3CH_2F$ was allowed to evaporate and the lower organic layer separated and analyzed to obtain the following on a $CF_3CH_2F$-free basis; 74.0% $CClF_2CH_2Cl$ and 25.9% $CHCl=CCl_2$. Small amounts (<0.1%) of other unidentified products were present.

These results show that the hydrogen fluoride which is combined with $CF_3CH_2F$ can react with $CHCl=CCl_2$ at a reduced catalyst loading and shorter reaction time than in Example 1.

Example 3

Reaction of Hydrogen Fluoride/1,1,1,2-Tetrafluoroethane with Trichloroethene

Example 2 was substantially repeated except that the reactor contents were heated to 100–105° C. for 15 minutes. Product analysis on a $CF_3CH_2F$-free basis showed 56.3% $CClF_2CH_2Cl$ and 43.6% $CHCl=CCl_2$.

Example 4

Reaction of Hydrogen Fluoride/2-Chloro-1,1,2-Tetrafluoroethane with tetrachloroethene The General Experimental Procedure for liquid-phase reactions was followed using $TaF_5$ (see Table 1), $CF_3CHClF$ (18 mL, 0.182 mol), anhydrous hydrogen fluoride (1.25 mL, 0.063 mol), the HF and $CF_3CH_2F$ amounts were selected so as to simulate an azeotropic composition, and $CCl_2=CCl_2$ (10.0 g, 0.06 mol). The reactor was pressurized to 200 psig when cold (−78° C.) with nitrogen. The back pressure regulator was set for 500 psig. The contents of the reactor were stirred and heated to the temperatures and for the times shown in Table 1. The reaction product was worked up as in Examples 1 to 3 and analyzed on a $CF_3CHClF$-free basis.

TABLE 1

| Reaction | | Cat. | Reaction Products | | |
|---|---|---|---|---|---|
| Time | Temp. | Wt. | % $CClF_2CHCl_2$ | % $CCl_2FCHCl_2$ | % $CCl_2=CCl_2$ |
| 1 h | 119–121° C. | 0.5 g | 1.2 | 54.3 | 43.9 |
| 1 h | 124–127° C. | 1.0 g | 4.2 | 57.3 | 37.3 |

Example 5

Reaction of Hydrogen Fluoride/Chlorodifluoromethane with Chloroform

The General Experimental Procedure for liquid-phase reactions was followed using $TaF_5$ (see Table 2), $CHClF_2$ (20 mL, 0.27 mol), anhydrous hydrogen fluoride (0.75 mL, 0.038 mol) and chloroform (10.0 g, 0.084 mol). The reactor was pressurized to 200 psig when cold (−78° C.) with nitrogen. The back pressure regulator was set for 500 psig. The contents of the reactor were stirred and heated to 69–71° C. for two hours. At run's end the reactor contents were cooled to room temperature and discharged onto ice. Most of the $CHCLF_2$ was allowed to evaporate and the lower organic layer separated and analyzed to obtain the following on a $CHClF_2$-free basis.

TABLE 2

| Cat. Wt. | % $CHCl_2F$ | % $CHCl_3$ |
|---|---|---|
| 0.5 g | 9.1 | 90.9 |
| 1.0 g | 11.2 | 88.8 |

Example 6

Reaction of Hydrogen Fluoride/1,1,1,2-Tetrafluoroethane with Trichloroethene

A ⅝" I.D. Inconel® reactor was charged with chrome oxide (60 mL, 78 g, 12/20 mesh) and heated to 275° C. in a flow of nitrogen (25 cc/min) for about 20 hours. The temperature was reduced to 175° C. and a 2:1 molar ratio of nitrogen and hydrogen fluoride was started through the reactor (total flow 100 ml/min). After one hour under these conditions, the molar ratio of nitrogen to hydrogen fluoride was adjusted to 1:3 and the temperature increased gradually over a two hour period to 400° C. The reactor was then brought back to the desired operating temperature, and flow of reactants (Table 3) started.

The product exiting the reactor was analyzed by gas chromatography. The table percentages are in mole %.

TABLE 3

| Temp. | Hydrogen Fluoride/ F134a[a]/ FC1120[b] | C.T.[c] | F134a | F133a[d] | F132b[e] | F1122[f] | FC1120 |
|---|---|---|---|---|---|---|---|
| 300° C. | .25/1/0.1* | 60 | 71 | 23 | 0 | 0 | 0 |
| 250° C. | .25/1/0.1 | 60 | 78 | 22 | 0 | 0 | 0 |
| 200° C. | .25/1/0.1 | 60 | 73 | 27 | 0 | 0 | 0 |
| 160° C. | .25/1/0.1 | 60 | 70 | 30 | 0 | 0 | 0 |
| 100° C. | .25/1/0.1 | 53 | 93 | 1 | 4 | 0 | 2 |
| 300° C. | .25/1/0.4 | 53 | 17 | 80 | 0 | 1 | 0 |
| 200° C. | .25/1/0.4 | 53 | 24 | 72 | 0 | 2 | 2 |
| 150° C. | .25/1/0.4 | 53 | 31 | 63 | 0 | 0.3 | 5 |
| 100° C. | .25/1/0.4 | 53 | 72 | 12 | 1 | 0 | 15 |

[a]. F134a = $CF_3CH_2F$
[b]. FC1120 = $CHCl=CCl_2$
[c]. C.T. = contact time in seconds
[d]. F133a = $CF_3CH_2Cl$
[e]. F132b = $CClF_2CH_2Cl$
[f]. F1122 = $CHCl=CF_2$
*molar ratio

What is claimed is:

1. A process wherein a halogenated hydrocarbon starting material is reacted with HF to produce a fluorination product including at least one product compound selected from the group consisting of saturated chlorofluorohydrocarbons and fluorohydrocarbons which contain from 1 to 6 carbon atoms, characterized by:

(1) fluorinating said starting material with HF to provide an initial product mixture containing HF and said at least one product compound, the amount of HF for said fluorination being in sufficient excess to azeotropically combine with said at least one product compound;

(2) distilling the initial product mixture of (1) to remove HCl and to recover said at least one product compound along with the HF which is azeotropically combined therewith;

(3) adding additional halogenated hydrocarbon material selected from (i) halocarbons of the formula $C_aH_bCl_cF_d$ where a is 1 to 6, b is 0 to 13, c is 1 to 13, and d is 0 to 13, provided that b+a+d equals 2a+2 when the compound is acyclic and 2a when it is cyclic, and (ii) halo-olefins of the formula $C_aH_bCl_cF_d$ where a is 2 to 6, b is 0 to 11, c is 1 to 11, and d is 0 to 11, provided b+c+d equals 2a when the compound is acyclic and 2a−2 when it is cyclic, to the azeotropic composition recovered in (2) to produce a reactive mixture, the amount of said additional halogenated hydrocarbon material being a molar amount greater than the HF in said azeotropic composition and said additional halogenated hydrocarbon being additional starting material; and (4) reacting the reactive mixture of (3) in the presence of a fluorination catalyst under fluorinating conditions to produce a product mixture with reduced HF content, thereby utilizing azeotropically combined HF.

2. The process of claim 1 wherein at least one product compound is selected from the group consisting of chlorofluorohydrocarbons.

3. The process of claim 1 wherein the at least one product compound is selected from the group consisting of fluorohydrocarbons.

4. The process of claim 1 wherein the at least one product compound has from 1 to 3 carbon atoms.

5. The process of claim 4 wherein the at least one product compound is selected from the group consisting of chlorofluorohydrocarbons.

6. The process of claim 4 wherein the at least one product compound is selected from the group consisting of fluorohydrocarbons.

7. The process of claim 1 wherein the at least one product compound has from 1 to 2 carbon atoms.

8. The process of claim 7 wherein the at least one product compound is selected from the group consisting of chlorofluorohydrocarbons.

9. The process of claim 7 wherein the at least one product compound is selected from the group consisting of fluorohydrocarbons.

10. The process of claim 1 wherein the product compound is selected for the group consisting of $CHClF_2$, $CF_3CHCl_2$ and $CF_3CHClF$.

11. The process of claim 1 wherein the product compound is selected from the group consisting of $CHF_2CHF_2$ and $CF_3CH_2F$.

12. The process of claim 1 wherein:

(1) $CCl_2=CCl_2$ is fluorinated with HF to produce an initial product mixture containing HF and at least one product compound selected from the group consisting of $CF_3CHCl_2$ and $CF_3CHClF$, the amount of HF for said fluorination being in sufficient excess to azeotropically combine with said at least one product compound;

(2) the initial product mixture of (1) is distilled to remove HCl and to recover said at least one product compound along with the HF which is azeotropically combined therewith;

(3) additional $CCl_2=CCl_2$ is added to the azeotropic composition recovered in (2) to produce a reactive mixture, the amount of said additional $CCl_2=CCl_2$ being a molar amount greater than the HF in said azeotropic composition; and (4) the reactive mixture of (3) is reacted in the presence of a fluorination catalyst under fluorinating conditions to produce a product mixture with reduced HF content, thereby utilizing azeotropically combined HF.

13. The process of claim 12 wherein in (1) olefinic impurities are produced and in (4) olefinic impurities produced in (1) are converted to saturated compounds.

14. The process of claim 1 wherein:
(1) $CHCl_3$ is fluorinated with HF to produce an initial product mixture containing HF and $CHClF_2$, the amount of HF for said fluorination being in sufficient excess to azeotropically combine with $CHClF_2$;
(2) the initial product mixture of (1) is distilled to remove HCl and to recover said $CHClF_2$ along with the HF which is azeotropically combined therewith;
(3) additional $CHCl_3$ is added to the azeotropic composition recovered in (2) to produce a reactive mixture, the amount of said additional $CHCl_3$ being a molar amount greater than the HF in said azeotropic composition; and
(4) the reactive mixture of (3) is reacted in the presence of a fluorination catalyst under fluorinating conditions to produce a product mixture with reduced HF content, thereby utilizing azeotropically combined HF.

15. The process of claim 1 wherein:
(1) $CHCl=CCl_2$ is fluorinated with HF to produce an initial product mixture containing HF and $CF_3CH_2F$, the amount of HF for said fluorination being in sufficient excess to azeotropically combine with said $CF_3CH_2F$;
(2) the initial product mixture of (1) is distilled to remove HCl and to recover said $CF_3CH_2F$ along with the HF which is azeotropically combined therewith;
(3) additional $CHCl=CCl_2$ is reacted to the azeotropic composition recovered in (2) to produce a reactive mixture, the amount of said additional $CHCl=CCl_2$ being a molar amount greater than the HF in said azeotropic composition; and
(4) the reactive mixture of (3) is reacted in the presence of a fluorination catalyst under fluorinating conditions to produce a product mixture with reduced HF content, thereby utilizing azeotropically combined HF.

16. The process of claim 15 wherein in (1) olefinic impurities are produced and wherein in (4) olefinic impurities produced in (1) are converted to saturated compounds.

17. The process of claim 1 wherein in (1) olefinic impurities are produced and wherein in (4) olefinic impurities produced in (1) are converted to saturated compounds.

18. A method for purifying 1,1,1,2-tetrafluoroethane product containing (a) $CF_3CH_2F$, (b) HF in an amount sufficient to azeotropically combine with said $CF_3CH_2F$, and (c) easily separated material including HCl, comprising:
separating HCl from said product; adding $CCl_2=CHCl$ to provide a reactive mixture containing $CF_3CH_2F$, HF and $CCl_2=CHCl$; and bringing the reactive mixture into contact with a fluorination catalyst in the vapor phase so as to decrease the hydrogen fluoride content.

19. The method of claim 17 wherein the 1,1,1,2-tetrafluoroethane product also contains (d) olefinic impurities which are converted to saturated compounds during said contact with a fluorination catalyst.

20. The method of claim 11 wherein the mole ratio of hydrogen fluoride to unsaturated compounds contacted with the fluorination catalyst is about 2.5:1; and wherein the fluorination catalyst is a fluorinated chrome oxide.

* * * * *